United States Patent [19]

Drews

[11] Patent Number: 5,258,011

[45] Date of Patent: Nov. 2, 1993

[54] CORNEAL RIVET

[76] Inventor: Robert C. Drews, 211 N. Meramec Ave., Clayton, Mo. 63105

[21] Appl. No.: 532,577

[22] Filed: Jun. 4, 1990

Related U.S. Application Data

[63] Continuation-in-part of Ser. No. 291,289, Dec. 28, 1988, Pat. No. 4,935,028, which is a continuation of Ser. No. 2,383, Jan. 12, 1987, abandoned.

[51] Int. Cl.$^5$ .............................................. A61B 17/00
[52] U.S. Cl. .................................... 606/220; 24/711.3; 24/711.4; 24/103; 411/517; 411/922
[58] Field of Search ............... 606/220, 232; 411/922, 411/517; 24/150 R, 150 P, 150 DP, 711.4, 711.3, 108, 103, 113

[56] References Cited

U.S. PATENT DOCUMENTS

| | | | |
|---|---|---|---|
| 350,622 | 10/1886 | Frank | 24/103 |
| 1,669,537 | 5/1928 | Schaffer | 606/232 |
| 1,848,318 | 3/1932 | Ciampi | 606/232 |
| 2,413,142 | 12/1946 | Jones et al. | 606/232 |
| 3,541,591 | 11/1970 | Hoegerman | 606/232 |
| 3,595,201 | 7/1971 | Oudenhoven | 606/117 |
| 3,910,281 | 10/1975 | Kletschka et al. | 606/232 |
| 3,976,079 | 8/1976 | Samuels et al. | 606/232 |
| 4,669,473 | 6/1987 | Richards et al. | 606/220 |
| 4,732,151 | 3/1988 | Jones | 606/220 |

Primary Examiner—Max Hindenburg
Assistant Examiner—Gary Jackson
Attorney, Agent, or Firm—Hugh D. Jaeger

[57] ABSTRACT

A corneal rivet for passing internally through the cornea and for providing closure of an incision in the cornea with a mechanically and optically configured rivet body including a first rivet head secured at one end thereto and a second member for securing to the other end of the rivet. The securing can either be through frictional engagement of the second member to the rivet body, through a knotting, a crimping, staking, threading, pinning, heat forming a ball or mushroom member, or a ratcheting engagement. The corneal rivet body can be utilized to suture other tissues besides the cornea, such as sclera, iris, other ocular tissues, skin, flesh, or the like.

3 Claims, 21 Drawing Sheets

CORNEAL RIVET

CROSS REFERENCES TO CO-PENDING APPLICATIONS

This application is a continuation-in-part of U.S. Ser. No. 07/291,289, filed Dec. 28, 1988, entitled "Corneal Rivet" now issued as U.S. Pat. No. 4,935,028, which is a continuation of U.S. Ser. No. 07/002,383, filed Jan. 2, 1987, entitled "Corneal Rivet" now abandoned, both to the same inventor.

BACKGROUND OF THE INVENTION

1. Field of the Invention

The present invention pertains to a surgical suture or wound closure technique, and more particularly, pertains to a corneal rivet for suturing and closing an incision in the cornea of the eye.

2. Description of the Prior Art

Corneal incisions have in the past been closed with the suture thread where the ophthalmic surgeon will carefully and with precision sew each suture thread about an incision through the cornea and subsequently tie the surgical knot. This is not only time consuming, but is also very delicate and intricate work requiring the utmost skill and facilities not only of the individual, but also an operating theater.

The present invention overcomes the disadvantages of the prior art by providing a corneal rivet for closing corneal wounds or corneal incisions which provides for mechanical, as well as optical closure of the wound.

SUMMARY OF THE INVENTION

The general purpose of the present invention is to provide a corneal rivet for closure of a corneal incision or corneal wound which provides mechanical and optical closure about the incision or wound for subsequent healing of the tissue.

According to one embodiment, there is provided a corneal rivet including a rivet body, a rivet head member affixed at one end, and a surgical needle affixed at the other end. The rivet body adjacent the surgical needle end subsequently engages into a second member and affixed thereto providing for mechanical and optical securement of the corneal tissue about the incision or wound. The securing to the second member can include frictional engagement, knotting of the rivet material, tying about a member, crimping, threading, pinning, heating to form an enlarged member or ratcheting. Also, the corneal rivet body can also be configured to secure into the corneal tissue for engagement in a reversed arched configuration as in FIG. 6B where the rivet material can be deformed or reformed at its exit from the tissue to become the securing member itself for a one-piece configuration.

A significant aspect and feature of the present invention includes a corneal rivet which can be made from biocompatible material and also biodegradable material. The corneal rivet can be pre-sterilized and packaged accordingly. The corneal rivet is cost effective.

Another significant aspect and feature of the present invention is a corneal rivet which requires minimal dexterity and skills for the insertion and utilization thereof.

Further significant aspects and features of the present invention is a corneal rivet which provides for mechanical closure of an incision or wound in the cornea and also provides for optical support at the site of insertion. Further, the corneal rivet in certain configurations may minimize stress and trauma about the incision.

Having thus described principal embodiments of the present invention, it is the principal object hereof to provide a corneal rivet for closing an incision or wound in the cornea.

One object of the present invention is a corneal rivet providing for mechanical, as well as optical closure of the cornea while minimizing stress and trauma to the corneal tissue.

Another object of the present invention is a corneal rivet which can also be used as a suture material for closing surgical incisions or wounds of body tissue.

Another object of the present invention is a corneal rivet which is effective in utilization requiring minimal skills and dexterity while providing for maximized surgical benefits.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

FIG. illustrates a perspective view of an internal corneal rivet, the present invention prior to a corneal insertion.

DESCRIPTION OF THE PREFERRED EMBODIMENTS

Figure 1:
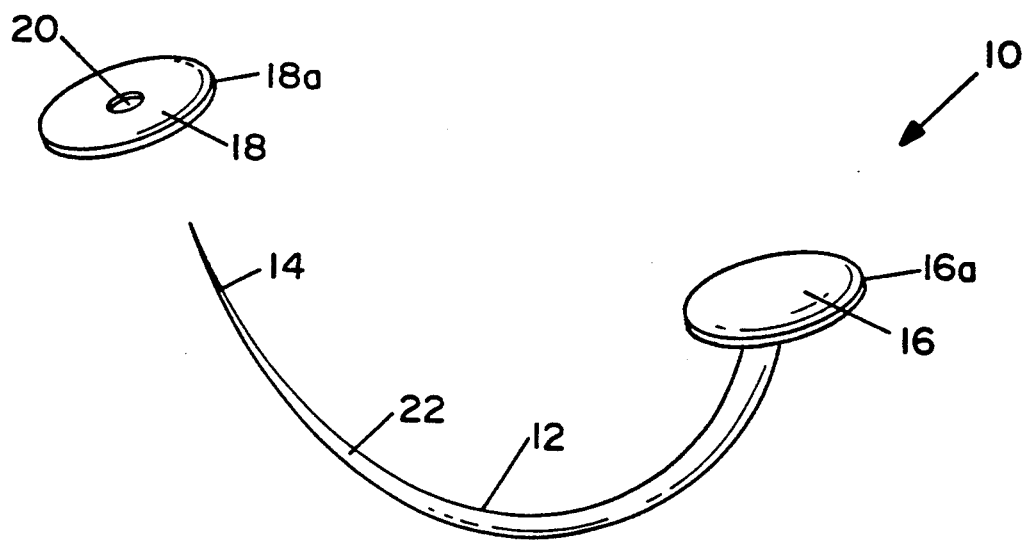

FIG. 1 illustrates a perspective view of an internal corneal rivet 10, the present invention, prior to insertion into a cornea including an arched configured metallic rivet body 12, a surgical needle tip 14 integral to the rivet body 12, and an oval or like shaped fixed rivet head member 16 including a smooth rounded edge 16a which is affixed obliquely to and integral to the end of the cylindrically shaped rivet body 12 and opposing the surgical needle 14. The degree of curvature of the rivet body 12 is determined by the corneal considerations. A second oval or suitably shaped end member 18 including a smooth rounded edge 18a is similar in shape to the fixed rivet head member 16, and includes a hole 20 which is aligned obliquely to the plane of the rivet head member 18 for accommodating the rivet body 12 at an angle of incidence similar to the oblique angle between the fixed rivet head member 16 and the rivet body 12. Rivet body 12 can include a slight taper 22 to provide for frictional engagement of the rivet body 12 within the hole 20 in the second rivet head member 18.

Figure 2:
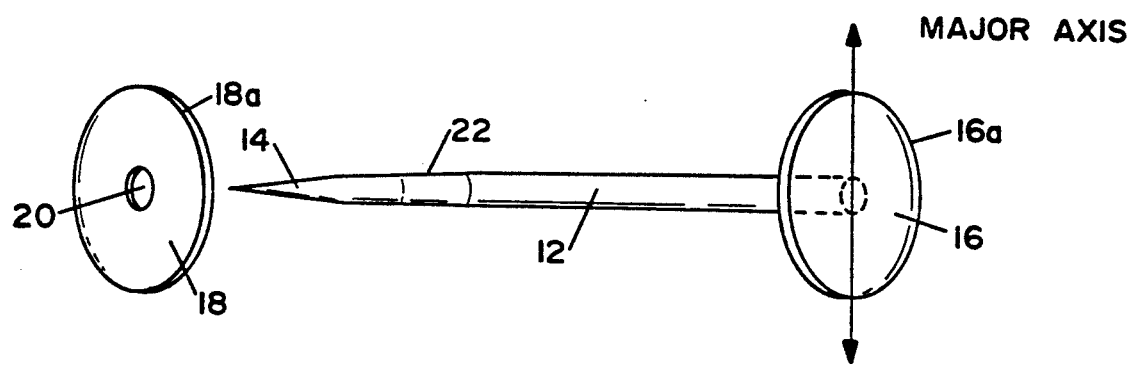
FIG. 2 illustrates a top view of the corneal rivet prior to corneal insertion.

FIG. 2 illustrates a top view of the corneal rivet 10 where all numerals correspond to those elements previously described. It is noted in particular that the major axis of the rivet head members 16 and 18 are perpendicular to the plane of the rivet body 12. Although the rivet head members are illustrated as ellipsoid or oval in shape by way of example and for purposes of illustration, they may also be round and the rivet head can take any other appropriate and suitable shape.

Figure 3:
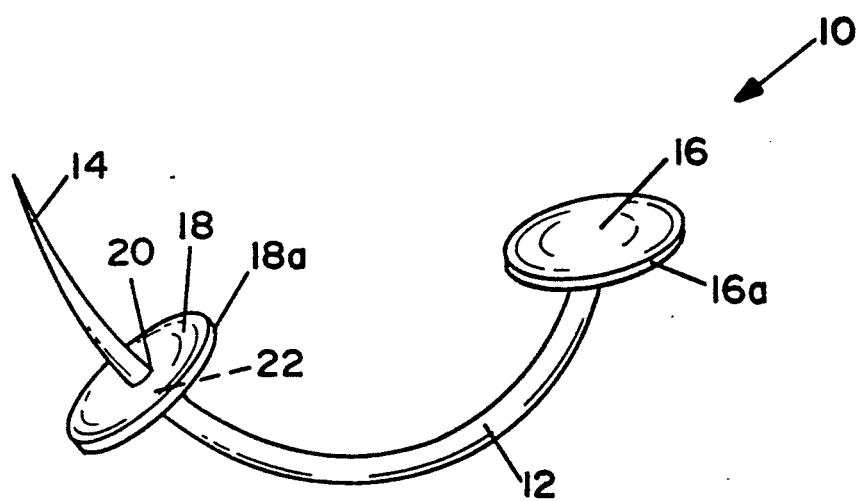
FIG. 3 illustrates a perspective view of the second rivet head engaged over the rivet body.

FIG. 3 illustrates a perspective view of the internal corneal rivet 10 where all numerals correspond to those elements previously described. Rivet head 18 is positioned having the surgical needle tip 14 engaged within hole 20, and seated over and about the rivet body 12 in the area of taper 22 for frictional engagement of the rivet head 18 over the rivet body 12. Subsequent to this frictional engagement, the surgical needle tip is trimmed flush to the top surface 18a as depicted in FIG. 4.

Figure 4:
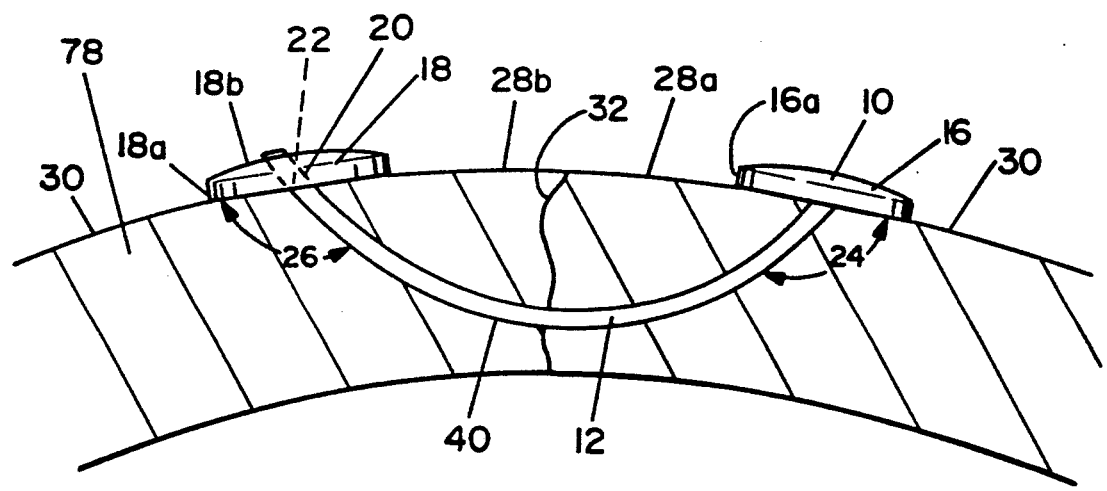
FIG. 4 illustrates a side elevation of an internal corneal rivet engaged in the cornea.

FIG. 4 illustrates a side view of the internal corneal rivet 10 engaged in the cornea 28 where all numerals correspond to those previously described Shown in particular are angles 24 and 26 described in FIG. 1 formed between the rivet body 12 and the rivet heads 16 and 18 which allow the overall vertical profile to remain as shallow and low as possible instead of utilizing an angle of incidence incurring a higher vertical profile of the rivet body. Angles 24 and 26 are preferably oblique for the application shown, but may be perpendicular or acute as needed. Rivet head members 16 and 18 lie in different planes as determined by angles 24 and 26 to effect proper bottom surface contact of rivet heads 16 and 18 with the outer corneal surface 30. The corneal rivet 10 is engaged within the cornea 28 holding and securing corneal portions 28a and 28b adjacent and against each other for healing along incision 32.

MODE OF OPERATION

Figure 5:
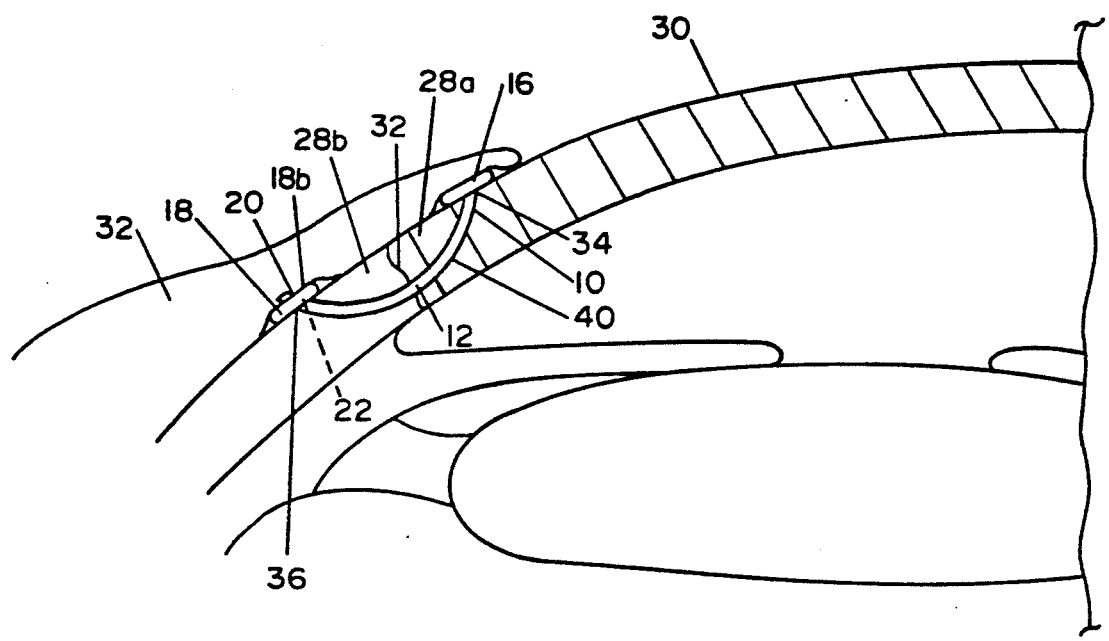
FIG. 5 illustrates a side elevation of an internal corneal rivet engaged in the cornea and beneath the conjunctiva.

FIG. 5 best illustrates the corneal rivet, the present invention, engaged in the cornea and beneath the conjunctival layer where all numerals correspond to those elements previously described. The corneal rivet 10 is inserted laterally across a corneal incision 32 using an ophthalmic needle holder. The corneal section members 28a and 28b are positioned against each other along the incision 32. The surgical needle tip 14 is inserted into corneal member 28a at point 34 laterally and somewhat downwardly through the incision 32, laterally and upwardly through corneal member 28b, and exiting at point 36 in corneal member 28b until the fixed rivet head member 16 firmly contacts the corneal surface 30 in and about the area of insertion 34. The second rivet head 18 is then positioned and oriented over the surgical needle tip and along the rivet body 12 until reaching the point of frictional engagement incurred when the hole 20 engages over and about the tapered area 22 on the rivet body 12 as described in FIG. 3. The surgical needle tip is then trimmed off adjacent to and as flush as possible to the top surface 18b of oval rivet head member 18 presenting as smooth a surface as possible to the conjunctiva 38. After an appropriate healing time, the corneal rivet may be removed by trimming off either the rivet heads 16 and 18, and sliding the rivet body out of the channel 40 created by insertion of the needle end 14 in which the rivet body is positioned during insertion and during the healing time.

The rivet body 12 including the surgical needle tip and end rivet members can be fashioned of stainless steel, titanium, platinum iridium, plastic, polypropylene, dacron, nylon, PMMA, polymers, or like biocompatible materials. The rivet body and end members can also be fashioned of biodegradable materials such as cat gut, biodegradable within a matter of days, collagen, biodegradable within one week, vicryl, biodegradable within six weeks, polydioxone, biodegradable within eight to twelve weeks or other biodegradable substances which could be biodegradable up to three months or longer. It should be noted that the biodegration times are given by way of example only, and that these times can be made to vary by manufacturing processes and will vary among patients as well.

The placement of the rivet can be anywhere in the cornea but generally is placed beneath the conjunctiva layer as illustrated.

The rivets can be inserted by ordinary instruments by an ophthalmic surgeon, such as with an ophthalmic needle holder. The rivets or rivet heads can have a "soft" flexible body such as cat gut, polypropylene, PMMA, nylon, flexible non-corrosive metallic strand, or the like, or may have a "hard" semi-rigid or rigid body such a stainless steel, titanium, platinum iridium or the like, and can also be fashioned of plastic, PMMA, or biodegradable materials.

ALTERNATIVE EMBODIMENTS

Figure 6A:
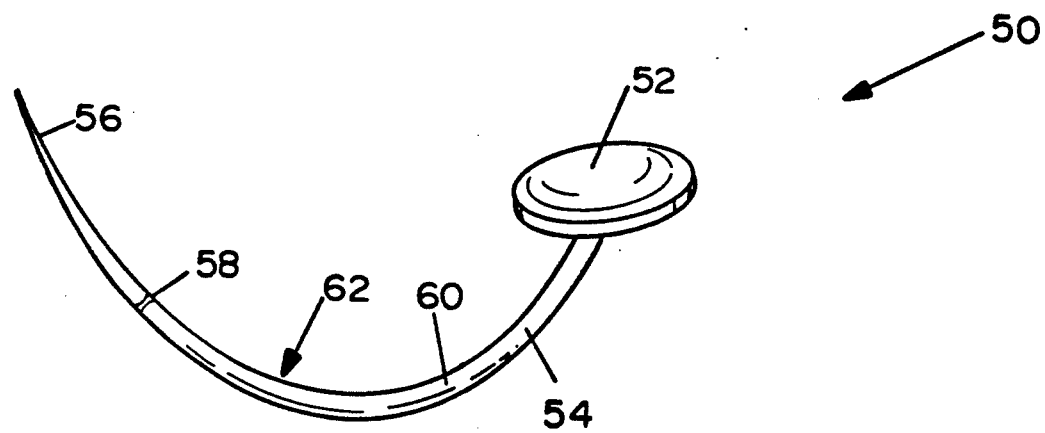
FIG. 6A and 6B illustrate a first alternative embodiment of a dual temper material rivet engaged in the cornea.
Figure 6B:
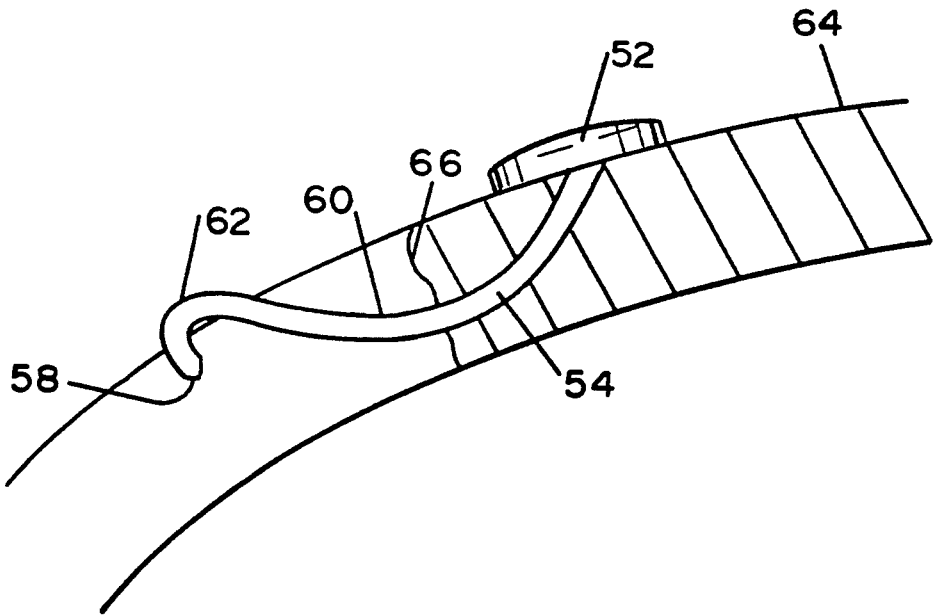

FIG. 6A and 6B illustrate a first alternative embodiment of a dual temper material rivet 50 including rivet head 52 and a rivet body 54. The rivet body 54 includes a surgical needle tip 56 consisting of a brittle or hard temper, a preweakened break off area 58, and a nonbrittle bendable soft temper portion 60 positioned between the break off point 58 and the rivet head 52. After insertion into the cornea as previously described, the surgical tip is severed or cut at the preweakened break off point 58, bent downwardly at point 62, and anchored into the cornea 64 across an incision 66 until such time as removal is necessitated after a proper healing period.

Figure 7:
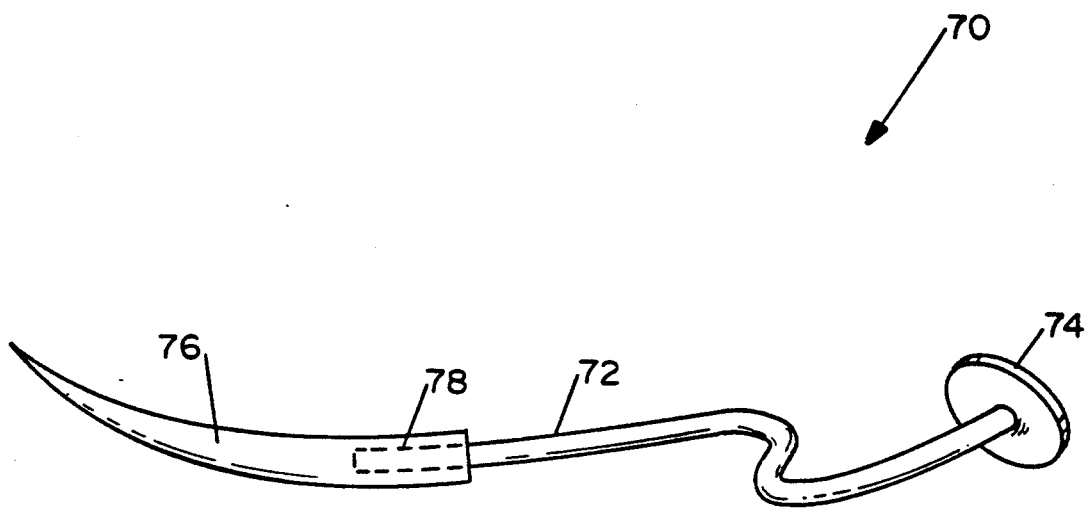
FIG. 7 illustrates a second alternative embodiment of a "soft" rivet body suture.

FIG. 7 illustrates a second alternative embodiment of an internal corneal rivet 70 utilizing a substantially "soft" rivet body or suture such as cat gut, polypropylene, PMMA, nylon, flexible metallic strand, or the like as opposed to the previously described "hard" rivet bodies. The soft corneal rivet is a flexible body 72 utilizing a flexible material such as cat gut, polypropylene, PMMA, nylon, flexible non-corrosive metallic strands, and includes an attached rivet head 74 and a surgical applicator needle 76. The flexible rivet body 72 is swaged or likewise affixed into a hole 78 at the end of the surgical needle 76.

The needle is inserted into the cornea as previously described in FIG. 5 until the fixed rivet head 74 positions on the outer corneal surface. The ophthalmic surgical needle is then severed from the flexible rivet body 72, and the rivet body 72 is attached to a second rivet head as later described in detail to form a corneal rivet with a soft rivet body and two rivet heads.

Figure 8:
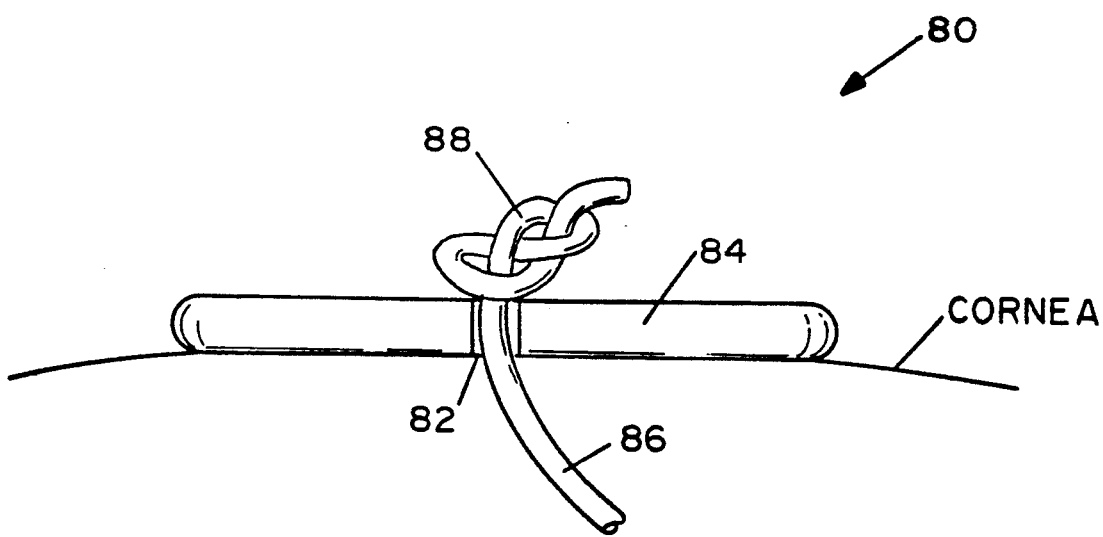
FIG. 8 illustrates a third alternative embodiment and method of affixing a soft rivet body to a second rivet head using a surgical knot.

FIG. 8 illustrates a third alternative embodiment illustrating fixation 80 of a soft rivet body to a second rivet head using a knot to secure a second rivet head 84 to a soft rivet body after insertion of the soft rivet body into and through the cornea. After the ophthalmic surgical needle 76 of FIG. 7 has passed through hole 82 in the second rivet 84, the needle 76 is severed from the flexible rivet body 86 and tied in a surgical or nautical figure eight knot 88 as illustrated to secure the rivet head 84 to the soft rivet body 86 of the corneal rivet. Hole 82 can be either perpendicular or oblique to the plane of the rivet head 84 based on the properties and usage of the flexible rivet body 86.

Figure 9A:
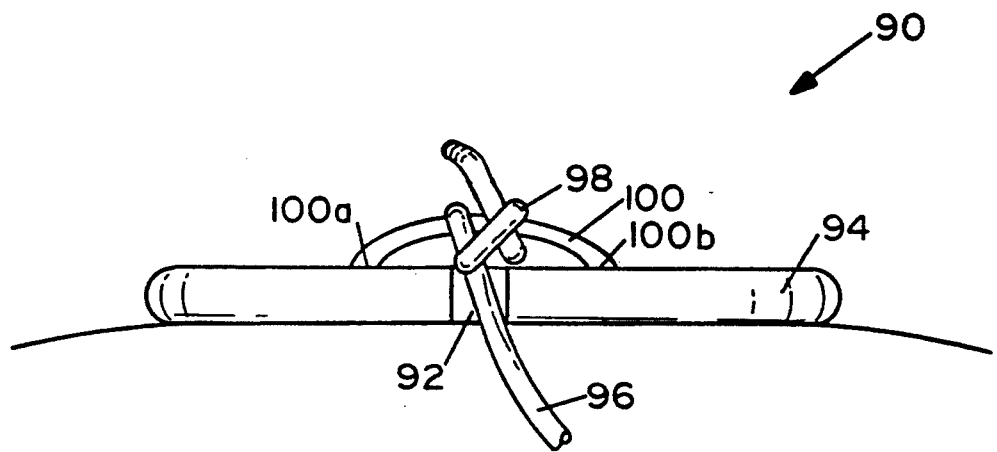
FIG. 9A illustrates a fourth alternative embodiment and method of affixing a soft rivet body to an arched anchor bar on a second rivet head.
Figure 9B:
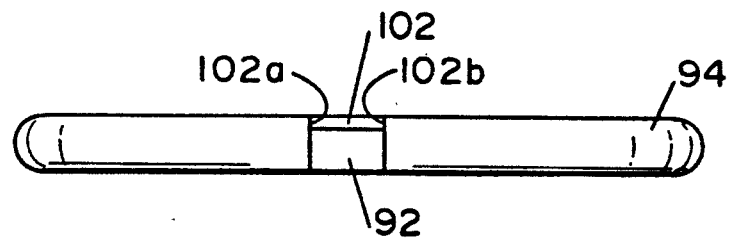
FIG. 9B illustrates a fifth alternative embodiment of a straight anchor bar and a second rivet head.

FIG. 9A and 9B illustrate fourth and fifth alternative embodiments illustrating fixation 90 of a soft rivet body to a second rivet head utilizing an arched anchor bar 100 and a knot to secure a second rivet head 94 to a soft rivet body 96 after insertion of the soft rivet body into and through the cornea. After the ophthalmic surgical needle has passed obliquely or perpendicularly through an oriented hole 92 in the second rivet head 94, the needle is severed from the flexible rivet body 96. The rivet body 96 secures utilizing an appropriate surgical knot 98 or rolling hitch to the arched anchor bar 100 which bridges hole 92 across the upper surface of rivet head 94 and which attaches integrally at points 100a and 100b. In the alternative, a straight anchor bar 102 attaches integrally to rivet head 94 at points 102a and 102b. The bar 102 is formed across the inner diameter of the rivet 94 offering a low profile anchor bar as illustrated in FIG. 9A.

Figure 10:
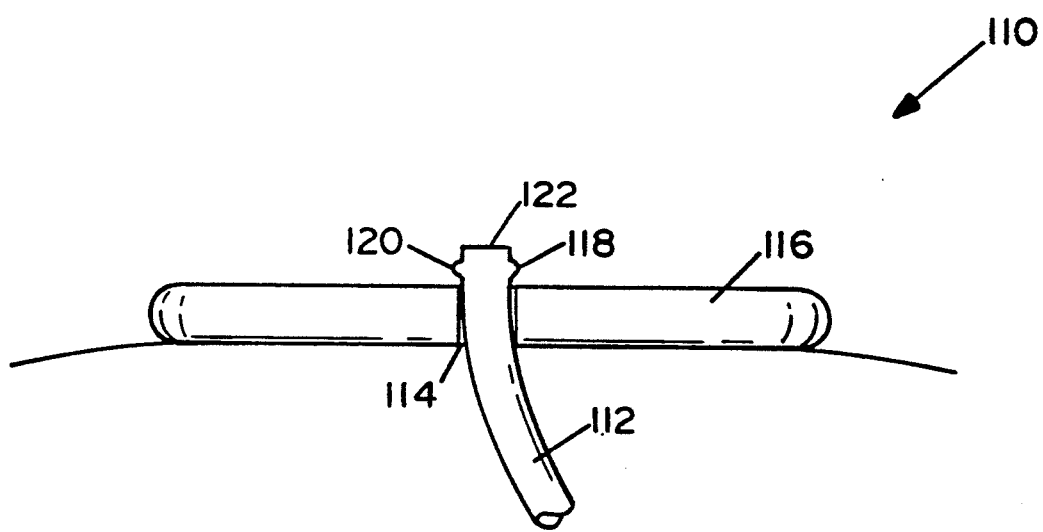
FIG. 10 illustrates a sixth alternative embodiment and method of affixing a soft or hard rivet body to a second rivet head by crimping.

FIG. 10 illustrates a sixth alternative embodiment illustrating fixation 110 by crimping a soft or hard rivet body to a second rivet head. After passage of the soft rivet body 112 through hole 114 in the second rivet head 116, a crimp is applied to the rivet body 112 above the upper surface of the rivet body 116 forming crimp nipples 118 and 120 securing the end 122 to the other members of the corneal rivet. A hard body rivet can be secured in the same manner. The hole 114 can also be drilled obliquely to the plane of the rivet head 116 for predetermined orientation.

Figure 11:
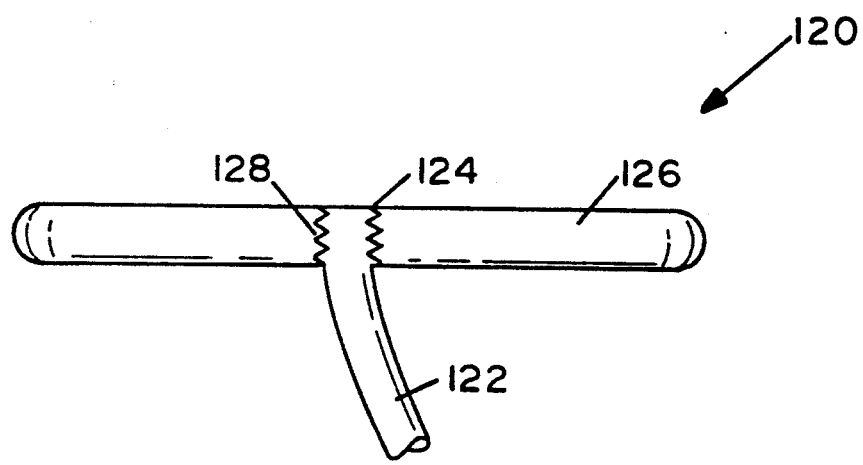
FIG. 11 illustrates a seventh alternative embodiment and method of affixing a soft rivet body to a second rivet head by heat staking.

FIG. 11 illustrates a seventh alternative embodiment illustrating fixation 120 of a soft or hard rivet body to a second rivet head by heat staking a rivet body into the rivet head. The rivet body 122 is inserted, and heat staked into hole 124 of a second rivet 126, thus integrally bonding the body 122 to the second rivet 126 along the inner circumference 128 of hole 124.

Figure 12:
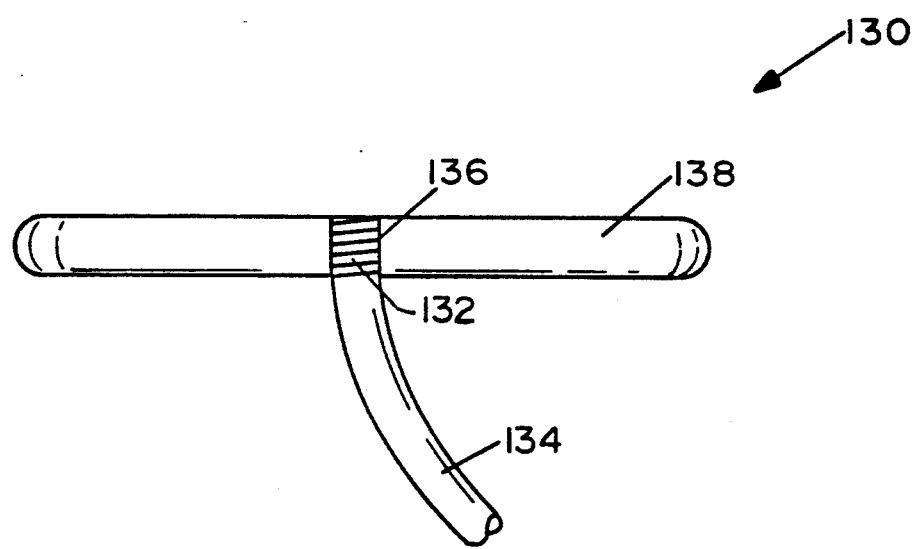
FIG. 12 illustrates an eighth alternative embodiment and method of affixing a threaded soft or hard rivet body to a threaded hole in a second rivet head.

FIG. 12 illustrates an eighth alternative embodiment illustrating fixation 130 of a soft or hard rivet body into a second rivet body. Threads 132 on soft rivet body 134 engage within a threaded hole 136 in a second rivet head 138 for securing the rivet head to the rivet body. The threaded hole 136 can also be oriented obliquely to accommodate a hard rivet body, but is not illustrated for sake of brevity.

Figure 13:
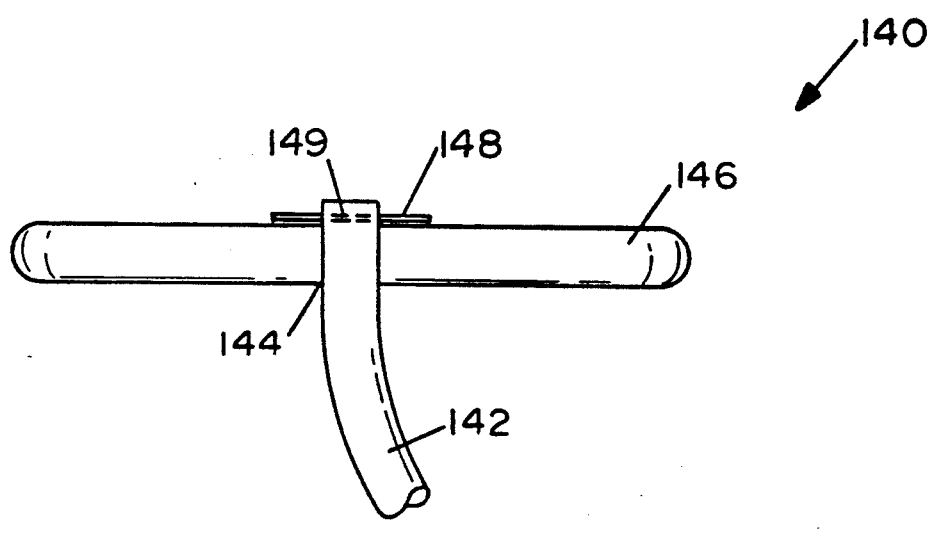
FIG. 13 illustrates a ninth alternative embodiment and method of affixing a soft or hard rivet body to a second rivet head by inserting a pin through the end of the rivet body.

FIG. 13 illustrates a ninth alternative embodiment illustrating fixation 140 of a soft or hard rivet body within a rivet head and secured therein by a pin. A flexible rivet body 142 engages within hole 144 in a second rivet head 146, and secures therein with a pin 148 through a hole 149 in the end of the flexible soft rivet body 142. A hard rivet body fixation is accomplished in the same like manner. Hole 144 can be obliquely oriented and the pin 148 can be passed through any series of holes in or near the end of the hard rivet body, or a hole can be created at surgery at the appropriate place in a soft rivet body.

Figure 14A:
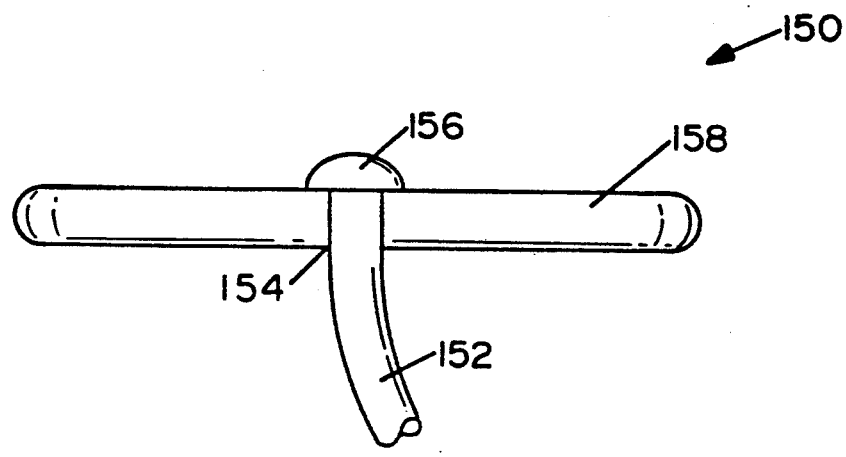
FIG. 14A illustrates a tenth alternative embodiment and method of affixing a soft rivet body to a second rivet head by creation of a mushroom shaped rivet body end.

FIG. 14A illustrates a tenth alternative embodiment illustrating fixation 150 of a soft rivet body to a second rivet head by heating the end of a polypropylene rivet body forming a mushroom shaped securement member to secure a flexible rivet to a second rivet head. A propylene, or other appropriate polymer rivet body 152 is passed through hole 154 as previously described and is heated by laser or other like techniques. Polypropylene for example when heated forms into a mushroom cap shaped securement member 156 as illustrated securing the rivet body 152 to the second rivet head 158.

Figure 14B:
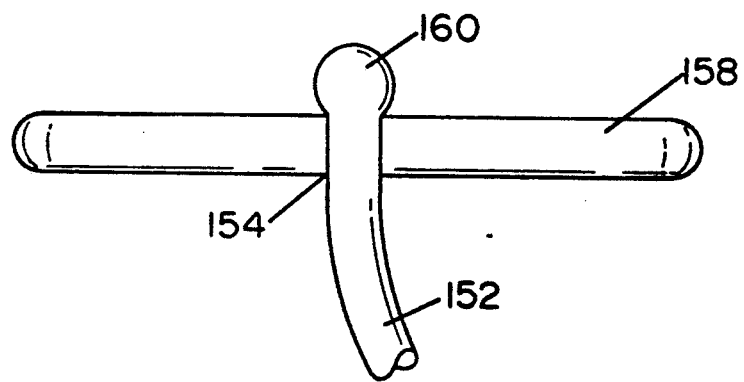
FIG. 14B illustrates an eleventh alternative embodiment and method of affixing a soft rivet body to a second rivet head by creation of a ball shaped rivet body end.

FIG. 14B illustrates an eleventh alternative embodiment illustrating a ball shaped securement member 160 as is formed by the use of other polymer which exhibit tendencies to ball when heated rather than mushroom when heated in FIG. 14A.

Figure 15:
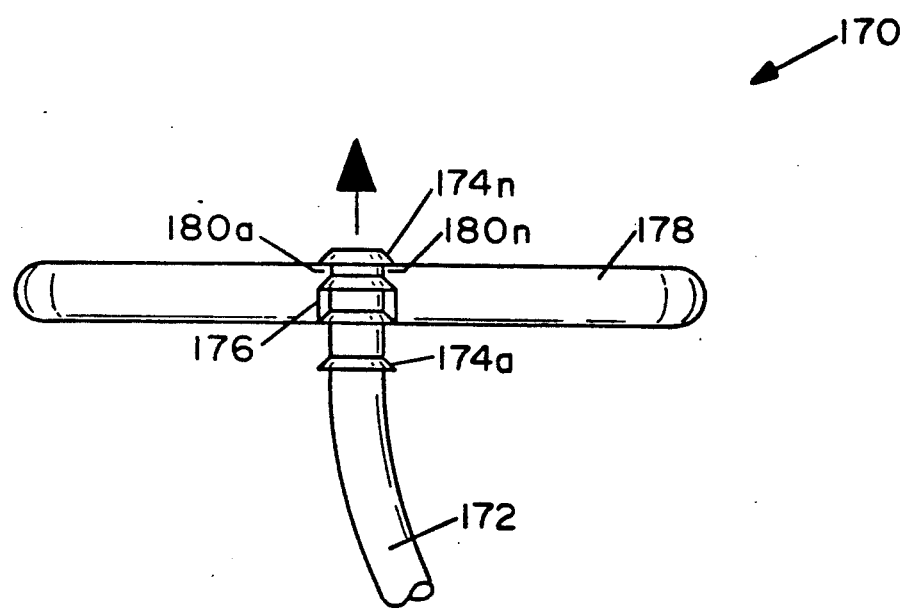
FIG. 15 illustrates a twelfth alternative embodiment and method of affixing a soft rivet body with ratchet teeth into a second rivet head with gripping teeth therein.

FIG. 15 illustrates a twelfth alternative embodiment illustrating fixation 170 of a soft rivet body to a second rivet head by ratchet teeth. A soft rivet body 172 with a plurality of annular ratchet teeth 174a-174n engages within a hole 176 in a second rivet head 178. Teeth 180a-180n near the upper surface of the rivet head 178 engage the ratchet teeth 174a-174n in the soft rivet body 172 for one way movement of the soft rivet body 172 through hole 176 in rivet head 178. An amount of adjustability in this method is obtained as the free end of the rivet body 172 is pulled through the hole 176 until the desired amount of tension from the fixed rivet head to the second rivet head and across the incision is obtained.

Figure 16:
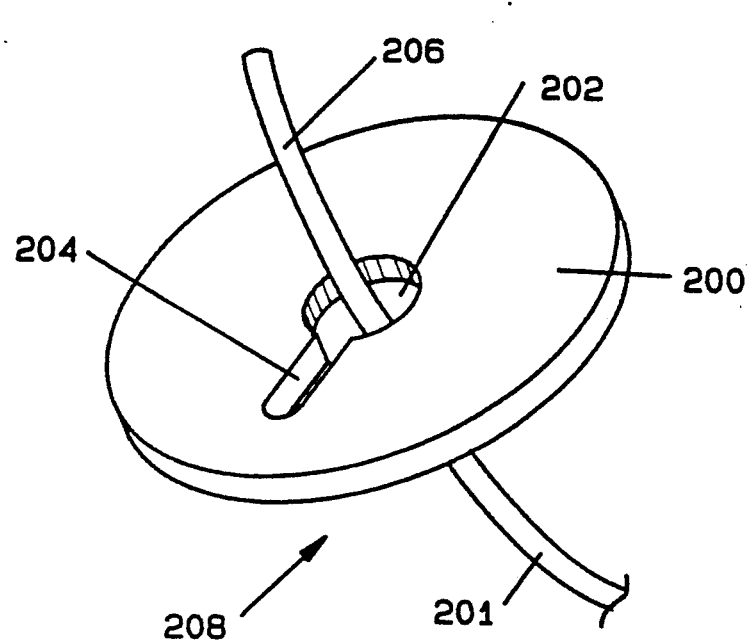
FIG. 16 illustrates a thirteenth alternative embodiment and method of affixing a rivet body using frictional engagement.

FIG. 16 shows a thirteenth alternative embodiment for affixing a rivet body. In this embodiment, the tip 206 of rivet body 201 is inserted into large diameter hole 202 of securing means 200. After proper alignment, securing means 200 is slidably moved in the direction of arrow 208 to cause frictional engagement of rivet body 201 with small diameter hole 204. This frictional engagement maintains the relative positions of rivet body 201 and securing member 200. Rivet body 201 may be a hard or soft rivet body, but the latter is preferred.

Figure 17:
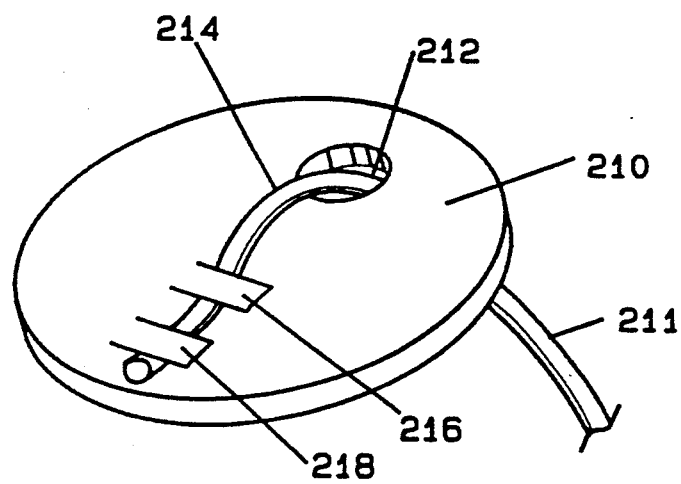
FIG. 17 illustrates a fourteenth alternative embodiment and method of affixing a rivet body using malleable tabs.

FIG. 17 illustrates a fourteenth alternative embodiment for affixing a rivet body. Rivet body 211 is inserted through aperture 212 in securing means 210. Rivet body 211 is bent at 214 to align with the plane of securing means 210. Malleable tabs 216 and 218 are bent over rivet body 211 as shown, thus frictionally engaging it.

Figure 18:
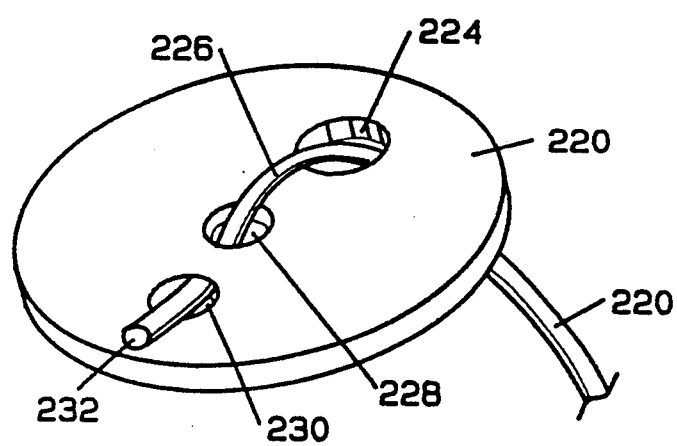
FIG. 18 illustrates a fifteenth alternative embodiment and method of affixing a rivet body using a turn buckle.

FIG. 18 is a fifteenth embodiment for affixing a rivet body. In this embodiment, rivet body 222 is alternately inserted through apertures 224, 228 and 230 of securing means 220 as shown. Tip 232 is cut flush with securing means 220.

Figure 19:
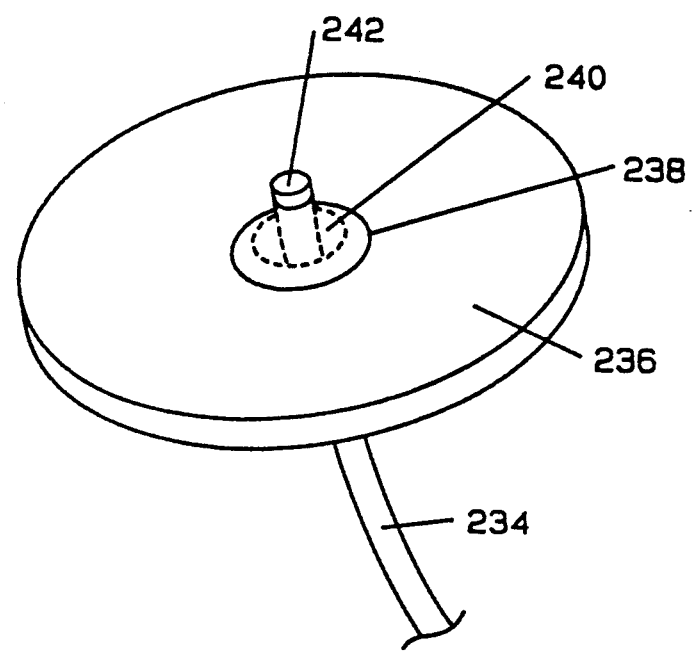
FIG. 19 illustrates a sixteenth alternative embodiment and method of affixing a rivet body using an adhesive.

FIG. 19 is a sixteenth embodiment for affixing a rivet body. In this embodiment, rivet body 234 is inserted into aperture 238 of a securing structure 236. An adhesive or glue 240 is applied to fix the position of rivet body 234 with respect to the securing structure 236. In the alternative, a crimping tool could be utilized to provide a mechanical bond between the rivet body and the securing structure. Any excess length of rivet body 234 is clipped forming tip 242. Rivet body 234 may be either of a soft or hard material.

Figure 20:
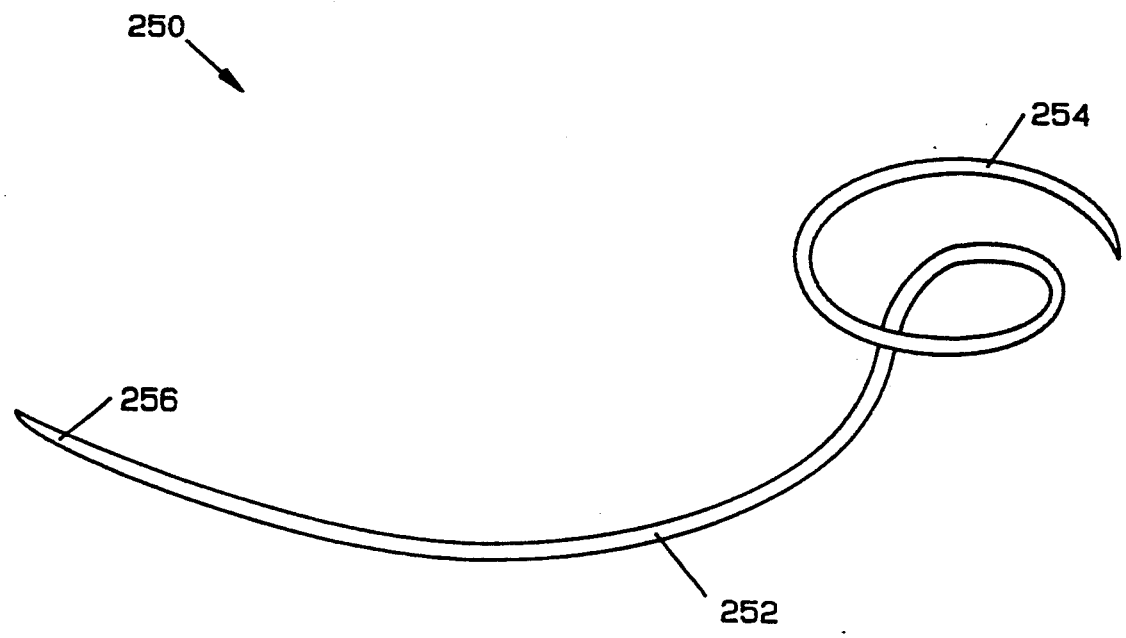
FIG. 20 illustrates an alternative embodiment of a one-piece spiral head corneal rivet; and, FIG. 21 illustrates an alternative embodiment of a one piece bent head corneal rivet.

FIG. 20 illustrates an alternative embodiment of a one-piece corneal rivet 250, including a rivet body 252 and a spiral rivet head 254 which is an extension of the rivet body 252. The rivet body 252 includes a tip 256 which can be fixated in a rivet head as previously described. The one-piece corneal rivet 250 may be either of a soft or hard material.

Figure 21:
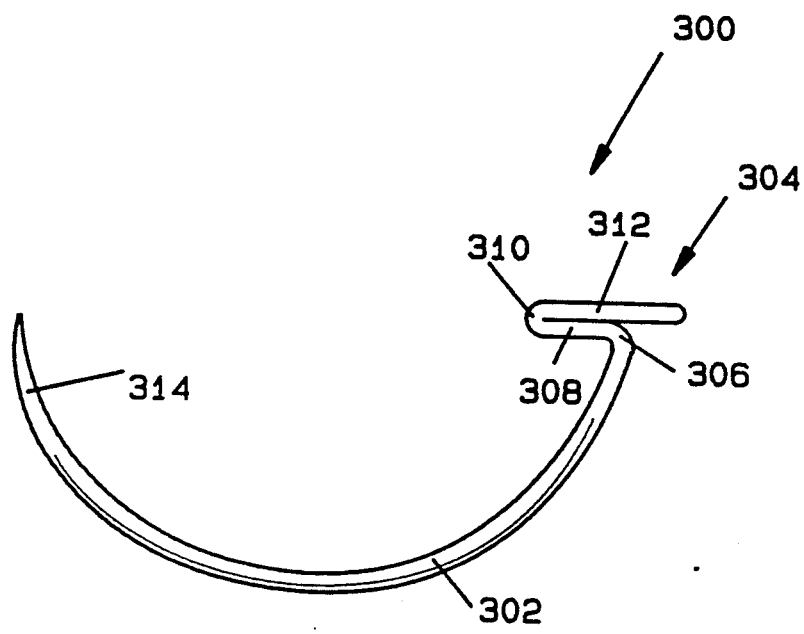

FIG. 21 illustrates an alternative embodiment of a one piece bent head corneal rivet 300 which includes a rivet body 302 and a bent rivet head 304 which is an extension of the rivet body 302. The rivet head 304 includes a first bend 306, a first straight portion 308, a second bend 310 at one end of the first straight portion 308, and another and second straight portion 312 starting at the bend 310 and aligning parallel to and immediately above and adjacent to the first straight portion 308. The rivet body 302 includes a tip 314 which can be fixated in a rivet head as previously described. The one piece rivet 300 may be either of a soft or hard material.

Various modifications can be made to the present invention without departing from the apparent scope hereof.

I claim:

1. Rivet for suturing an closing a bodily incision comprising:
    a. a configured arched body having a bodily surface penetrating end and a bodily surface engaging end;
    b. a first rivet head member secured to said bodily surface engaging end of said configured arched body, said head member having a flat bodily surface engaging portion and a thickness small relative to its diameter;
    c. a securing means for securing said configured arched body bodily surface penetrating end once said penetrating end has exited said body, said securing means comprising a second rivet head member having a flat bodily surface engaging portion and having frictional engaging means for engaging said configured arched body bodily surface penetrating rod; and
    d. said frictional engaging means further comprising a large diameter aperture through said second rivet head member and having a diameter larger than the diameter of said configured arched body bodily surface penetrating end for slidable insertion of said configured arched body bodily surface penetrating end and a communicating small diameter aperture through said second rivet head member for frictionally engaging said configured arched body bodily surface penetrating end.

2. Rivet for suturing an closing a bodily incision comprising:
    a. a configured arched body having a bodily surface penetrating rod end tapered along a portion of said body, and a bodily surface engaging end;
    b. a first rivet head member with rounded edges secured to said bodily surface engaging end of said configured arched body, said head member having a flat bodily surface engaging portion and a thickness small relative to its diameter; and,
    c. a securing means for securing said configured arched body bodily surface penetrating end once said penetrating end has exited said body, said securing means comprising a second rivet head member having a flat bodily surface engaging portion and having frictional engaging means for engaging said covered portion of said configured arched body bodily surface penetrating rod.

3. Rivet for suturing an closing a bodily incision comprising:
    a. a configured arched body having a bodily surface penetrating rod end tapered along a portion of said body and a bodily surface engaging end;
    b. a first rivet head member secured to said bodily surface engaging end of said configured arched body, said head member having a flat bodily surface engaging portion and a thickness small relative to its diameter; and,
    c. a securing means for securing said configured arched body bodily surface penetrating end once said penetrating end has exited said body, said securing means comprising a second rivet head member with rounded edges having a flat bodily surface engaging portion and having frictional engaging means for engaging said tapered portion of said configured arched body bodily surface penetrating rod.

* * * * *